United States Patent
Kaplan et al.

(10) Patent No.: US 10,226,545 B2
(45) Date of Patent: Mar. 12, 2019

(54) NEW-GENERATION FLUID PARTICLE DIFFUSER

(71) Applicant: CEKK KOKU VE KOZMETIK LTD. STI., Istanbul (TR)

(72) Inventors: Cem Kaplan, Istanbul (TR); Ertan Korkmaz, Istanbul (TR)

(73) Assignee: CEKK KOKU VE KOZMETIK LTD. STI, Istanbul (TR)

( * ) Notice: Subject to any disclaimer, the term of this patent is extended or adjusted under 35 U.S.C. 154(b) by 289 days.

(21) Appl. No.: 15/171,154

(22) Filed: Jun. 2, 2016

(65) Prior Publication Data
US 2016/0339461 A1 Nov. 24, 2016

Related U.S. Application Data

(63) Continuation-in-part of application No. 13/814,099, filed as application No. PCT/TR2011/000005 on Jan. 10, 2011, now abandoned.

(30) Foreign Application Priority Data

Aug. 9, 2010 (TR) .................................. 2010 06515

(51) Int. Cl.
| | | |
|---|---|---|
| A61L 9/12 | (2006.01) | |
| A61L 9/14 | (2006.01) | |
| A61M 11/02 | (2006.01) | |
| A61M 11/00 | (2006.01) | |
| A01M 1/20 | (2006.01) | |
| A61M 15/08 | (2006.01) | |

(52) U.S. Cl.
CPC .............. *A61L 9/12* (2013.01); *A01M 1/2038* (2013.01); *A01M 1/2055* (2013.01); *A61L 9/14* (2013.01); *A61M 11/003* (2014.02); *A61M 11/02* (2013.01); *A61L 2209/10* (2013.01); *A61L 2209/134* (2013.01); *A61L 2209/135* (2013.01); *A61M 15/08* (2013.01)

(58) Field of Classification Search
CPC ........... A61L 9/12; A61L 9/14; A61M 11/003; A61M 11/02
See application file for complete search history.

(56) References Cited

U.S. PATENT DOCUMENTS

| | | | |
|---|---|---|---|
| 2,520,368 A | 8/1950 | Landau | |
| 4,084,732 A | 4/1978 | Dearling | |
| 4,606,477 A | 8/1986 | Spengler | |
| 6,405,944 B1* | 6/2002 | Benalikhoudja | A61L 9/145 128/200.18 |
| 2002/0068023 A1* | 6/2002 | Davis | A61L 9/12 422/124 |
| 2008/0087692 A1* | 4/2008 | Yu | B05B 11/0029 222/633 |

(Continued)

FOREIGN PATENT DOCUMENTS

GB 1028788 A 5/1966

*Primary Examiner* — Ryan A Reis
(74) *Attorney, Agent, or Firm* — Egbert Law Offices, PLLC

(57) ABSTRACT

A new-generation GMP (Good Manufacturing Practice) compliant hygienic fluid particle diffuser allowing to release the particles of fluids such as bottled drugs, extracts and natural oils by generating a particular pressure without any heating process without degrading the essence of the fluid thanks to a disposable fluid chamber.

4 Claims, 2 Drawing Sheets

(56) References Cited

U.S. PATENT DOCUMENTS

Figure 1:
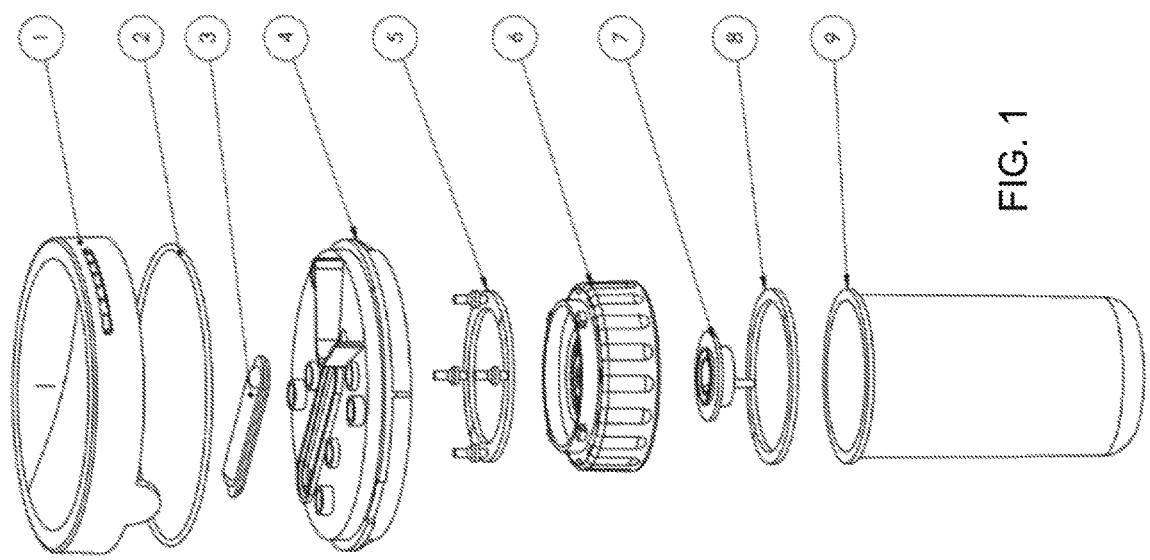
Figure 2:
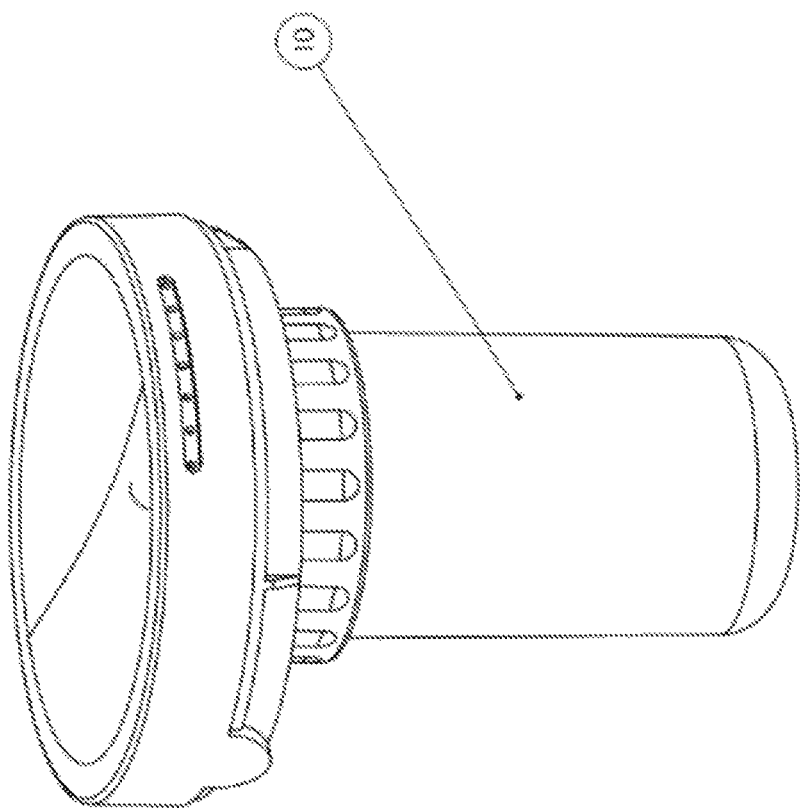

2008/0251953 A1* 10/2008 Robert ................ A61L 9/14
                                                                        261/78.2
2011/0089252 A1* 4/2011 Rosener ............. A01M 1/2044
                                                                        239/6

* cited by examiner

NEW-GENERATION FLUID PARTICLE DIFFUSER

CROSS-REFERENCE TO RELATED U.S. APPLICATIONS

The present application is a continuation-in-part of U.S. application Ser. No. 13/814,099, filed on Feb. 4, 2013, entitled "Enhanced Micro Particles Drug and Odor Diffusion Apparatus," presently pending.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a new-generation fluid particle diffuser allowing to release, without the use of heating and repellent gas, the particles of fluids such as bottled drugs, extracts and natural oils, by generating a particular pressure via a special channel and feeder system without degrading the essence of the fluid, and employing disposable tubes to for utmost hygiene.

2. Description of Related Art Including Information Disclosed under 37 CFR 1.97 and 37 CFR 1.98

Particles released by conventional diffusers today are in the form of short-term and heavy particles, and fail to ensure long-term retention and diffusion on site. In addition, each of the commercially available products is sold in a same chamber or in a configuration without a special locking system allowing for convenient filling externally. Although products appear to be sealed, they can be disassembled and filled externally, including the end user. On the other hand, our system is capable of ensuring hygiene thanks to the disposable use, wherein mixing with other fluids is avoided, and hence combination with various fluids is possible.

Purpose of the Invention:

Thanks to the new-generation fluid particle diffuser of the present invention, uniform diffusion of bottled fluid particles is ensured by controlling the air and pressure system without heating and use of any repellent gas. As particles released in selective quantities do not precipitate like aerosol, they can remain suspended in air for long time, and preserve their quality both in bottled form and during on-site storage. Furthermore, disposable use contemplated by the invention ensures hygiene and allows combination with various fluids. Hence, hygienic, versatile, cost-effective and high-quality diffusion is ensured.

BRIEF SUMMARY OF THE INVENTION

The present invention is a new-generation GMP (Good Manufacturing Practice) compliant hygienic fluid particle diffuser allowing to release the particles of fluids such as bottled drugs, extracts and natural oils by generating a particular pressure without any heating process without degrading the essence of the fluid thanks to a disposable fluid chamber.

BRIEF DESCRIPTION OF THE SEVERAL VIEWS OF THE DRAWINGS

FIG. 1 is the exploded/unassembled view of the diffuser.

FIG. 2 is the assembled view of the diffuser.

Parts referred to in the drawings:

1—Micron granulator top bottle locking, shaking and fluid micron dispensing unit

2—O-ring avoiding pressure and fluid leak off the fluid chamber

3—Air pressure stabilizer/regulator

4—Micron granulator bottom bottle locking assembly bottom and air inlet and channel

5—O-ring avoiding pressure and fluid leak off the disposable fluid chamber

6—Micron granulator pressurized air inlet and top bottle locking assembly

7—Micron granulator and fluid drawing chamber/area

8—O-ring avoiding pressure and fluid leak off the fluid chamber

9—Fluid chamber

10—Micron granulator

DETAILED DESCRIPTION OF THE INVENTION

The present invention relates to disposable chambers allowing to release, without the use of heating and repellent gas, the particles of fluids such as bottled drugs, extracts and natural oils, by generating a particular pressure, and further to a new-generation fluid particle diffuser capable of diffusing different fluids and solvents. The invention is characterized with a micron granulator top bottle locking, shaking and fluid micron dispensing nozzle/holes (1), a first O-ring (2), an air pressure stabilizer/regulator (3), a micron granulator bottom bottle locking assembly bottom and air inlet and channel (4), a second O-ring (5), a micron granulator pressurized air inlet and top bottle locking assembly (6), a micron granulator and fluid drawing chamber/area (7), a third O-ring (8), and a water chamber (9). FIG. 2 shows the micron granulator (10) constituting the assembled form/whole assembly of the foregoing parts. Each of the O-rings avoids pressure and fluid leak off the disposable fluid chamber The invention has been designed as a system capable of releasing and/or diffusing all fluid forms, without the use of heating and ultrasonic operation, liquid human drugs, medicinal aroma therapy oils, pesticides, etc., only by employing pneumatic force/pressure in its micron granulator and fluid drawing chamber/area (7) designed to have a special diameter and inclination to granulate the particles into a size of <1 micron (0.1 mm-0.6 mm).

Principle of Operation:

Special fluid mixtures prepared are placed in the fluid chamber (9), and then third O-ring (8), micron granulator and fluid drawing chamber/area (7), and micron granulator pressurized air inlet and top bottle locking assembly (6) are assembled into a compact/monoblock filling unit.

Thanks to its special locking mechanism, this special filling unit avoids reopening and refilling, and hence has the quality of a GMP (Good Manufacturing Process) compliant product.

Specially prepared mixtures are then assembled and locked to the micron granulator bottom bottle locking assembly bottom and air inlet and channel (4), and micron granulator top bottle locking, shaking and fluid micron particle dispenser (1). Then, the fluid particle diffuser starts to function with the stabilized/regulated pressurized air fed by this part.

In thermal systems, despite molecules lose their functionality due to heat, odour molecules retain their function under cooled air. Thus, fluid composition remains intact, and micron granulator (4) performs a process where particles are evenly distributed.

While air supplied to the micron granulator allows drawing the fluid upwards by means of the pulling force due to the special inclination inside, it also moves the fluid via said inclination through the bottom hole at a faster pressure, resulting in granulation into a size of <0.1 microns through a specific angular hole and along a specially functional path, thereby transforming the fluid into microns that are lighter than gas. And these microns which are lighter than gas are released through the top inlet together with air that has accumulated inside the bottle.

Air is lubricated by means of the specially angled micron granulator and drawing chamber/area (7), and hence, with the stabilized/regulated air, release of fluid particles runs as a controlled process at desired intervals without degrading the fluid quality and with longer retention on site.

Air pressure stabilizer/regulator (3) allows optional distance adjustment for release at desired time for any huge or small area/site desired.

Model has been designed with a disposable configuration.

The model set into a compact/monoblock unit with the locking mechanism does not allow reuse and refilling of a different type of fluid, hence ensures safe use.

Thanks to the disposable configuration, replacement with another product or other product groups is possible upon depletion. Thanks to the disposable configuration, when the product is depleted, it may be replaced and another type of fluid may be added. For instance, a medicinal drug added after a pesticide may safely be used. And this is possible with a GMP-compliant disposable system allowing for special filling in a separately sold unit.

We claim:

1. A fluid particle diffuser that allows for a release of particles from fluids by generating a pressure, the fluid particle diffuser comprising:
    a fluid chamber;
    a granulator top having fluid dispensing holes therein;
    a first O-ring joined to said granulator top;
    an air pressure regulator;
    a first locking assembly having an air inlet and a channel, said granulator top affixed to said first locking assembly such that said first O-ring and said air pressure regulator are interposed therebetween, said air pressure regulator cooperative with said air inlet and said channel so as to control a flow of air therethrough;
    a second O-ring;
    a second locking assembly joined to an underside of said first locking assembly, said second O-ring interposed in sealing relation between said first and second locking assemblies;
    a granulator and fluid drawing element cooperative with said second locking assembly; and
    a third O-ring interposed between said second locking assembly and said fluid chamber, said second locking assembly being locked to a top of said fluid chamber.

2. The fluid particle diffuser of claim 1, said granulator and fluid drawing element having an inclination and diameter adapted to granulate the particles to a diameter of less than one micron.

3. The fluid particle diffuser of claim 1, said third O-ring, said granulator and fluid drawing area, and said first and second locking assemblies are arranged in a locked unit.

4. The fluid particle diffuser of claim 1, wherein said air pressure regulator is adapted to release fluid particles toward a desired area.

\* \* \* \* \*